United States Patent
Yokoyama et al.

(10) Patent No.: US 6,893,847 B2
(45) Date of Patent: May 17, 2005

(54) **OLIGONUCLEOTIDE FOR DETECTING *SALMONELLA* AND METHOD OF DETECTING *SALMONELLA***

(75) Inventors: Akihiro Yokoyama, Sagamihara (JP); Takahiko Ishiguro, Yokohama (JP)

(73) Assignee: Tosoh Corporation, Shinnanyo (JP)

( * ) Notice: Subject to any disclaimer, the term of this patent is extended or adjusted under 35 U.S.C. 154(b) by 295 days.

(21) Appl. No.: 10/046,313

(22) Filed: Jan. 16, 2002

(65) Prior Publication Data

US 2003/0113736 A1 Jun. 19, 2003

(30) Foreign Application Priority Data

Jan. 17, 2001 (JP) ........................................ 2001-009464

(51) Int. Cl.$^7$ .......................... C12P 19/34; C07H 21/04
(52) U.S. Cl. ...................... 435/91.51; 6/91.1; 536/23.1; 536/24.3; 536/24.33
(58) Field of Search ....................... 435/6, 91.1, 91.51; 536/23.1, 24.3, 24.33

(56) References Cited

U.S. PATENT DOCUMENTS 5,409,818 A    4/1995 Davey et al.

FOREIGN PATENT DOCUMENTS

| EP | 0 373 960 | 6/1990 |
|---|---|---|
| EP | 0 969 101 | 1/2000 |
| JP | 2650159 | 9/1997 |
| WO | WO 99/58713 | 11/1999 |

OTHER PUBLICATIONS

Johansen et al. (Abstracts of the General Meeting of the American Society for Microbiology (2001) 101: 576).*
Simpkins et al. (Journal of Microbiological Methods (1999) 38(3): 218).*
G. Jenikova, et al., International Microbiology, vol. 3, No. 4, pp. 225–229, XP–001079778, "Detection of *Salmonella* in Food Samples by the Combination of Immunomagnetic Separation and PCR Assay", Dec. 2000.

C.–H. Chiu, et al., Journal of Clinical Microbiology, vol. 34, No. 10, pp. 2619–2622, XP–001083638, "Rapid Identification of *Salmonella serovars* in Feces by Specific Detection of Virulence Genes, *InvA* and *spvC*, by an Enrichment Broth Culture–Multiplex PCR Combination Assay", Oct. 1996.

S. A. Simpkins, et al., Letters in Applied Microbiology, vol. 30, No. 1, pp. 75–79, XP–001084964, "An RN a Transcription–Based Amplification Technique (NASBA) for the Detection of Viable *Salmonella enterica*", Jan. 2000.

A. R. Bennett, et a., Letters in Applied Microbiology, vol. 26, pp. 437–441, XP–001083614, "Rapid and Definitive Detection of Salmonella in Foods by PCR", 1998.

L. Cocolin, et al., Letters in Applied Microbiology, vol. 85, pp. 673–677, XP–001083629, "Use of Polymerase Chain Reaction and Restriction Enzyme Analysis to Directly Detect and Identify *Salmonella typhimurium* in Food", 1998.

T. Ishiguro, et al., Nucleic Acids Research, vol. 24, No. 24, pp. 4992–4997, "Fluorescence Detection of Specific Sequence of Nucleic Acids by Oxazole Yellow–Linked Oligonucleotides. Homogeneous Quantitive Monitoring of in Vitro Transcription", Jul. 30, 1996.

J.E. Galan, et al., Journal of Bacteriology, vol. 174, No. 13, pp. 4338–4349, "Molecular and Functional Characterization of the *Salmonella* Invasion Gene *invA*: Homology of InvA to Members of a New Protein Family", Feb. 10, 1992.

* cited by examiner

*Primary Examiner*—Carla J. Myers
*Assistant Examiner*—Alexander H. Spiegler
(74) *Attorney, Agent, or Firm*—Oblon, Spivak, McClelland, Maier & Neustadt, P.C.

(57) ABSTRACT

The present invention provides oligonucleotides for detecting *Salmonella* toxin gene invA mRNA and stn mRNA which oligonucleotides specifically bind to invA mRNA or stn mRNA at a relatively low temperature (for example, 41° C.) and at a constant temperature, and a process of amplifying *Salmonella* toxin gene invA mRNA or stn mRNA and a method of detecting the same using the oligonucleotides.

14 Claims, 5 Drawing Sheets

Fig.3
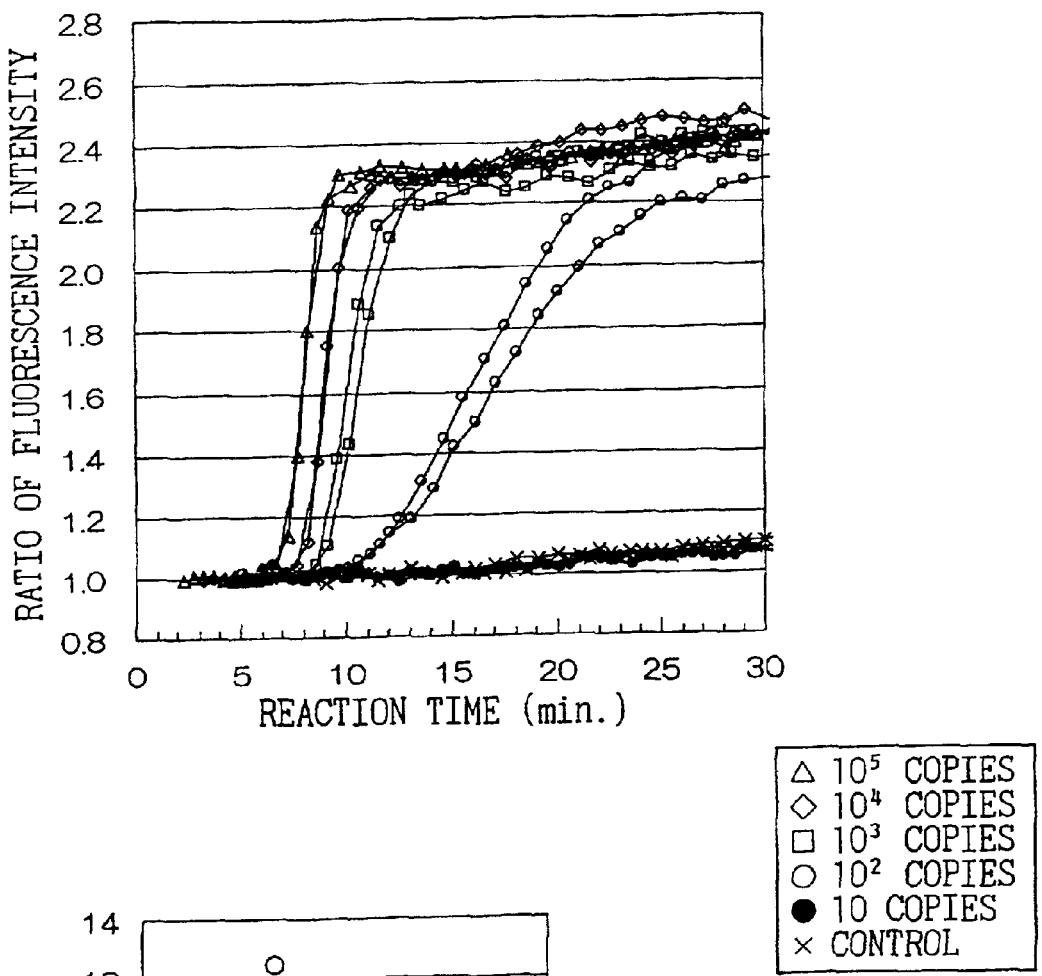
(a)
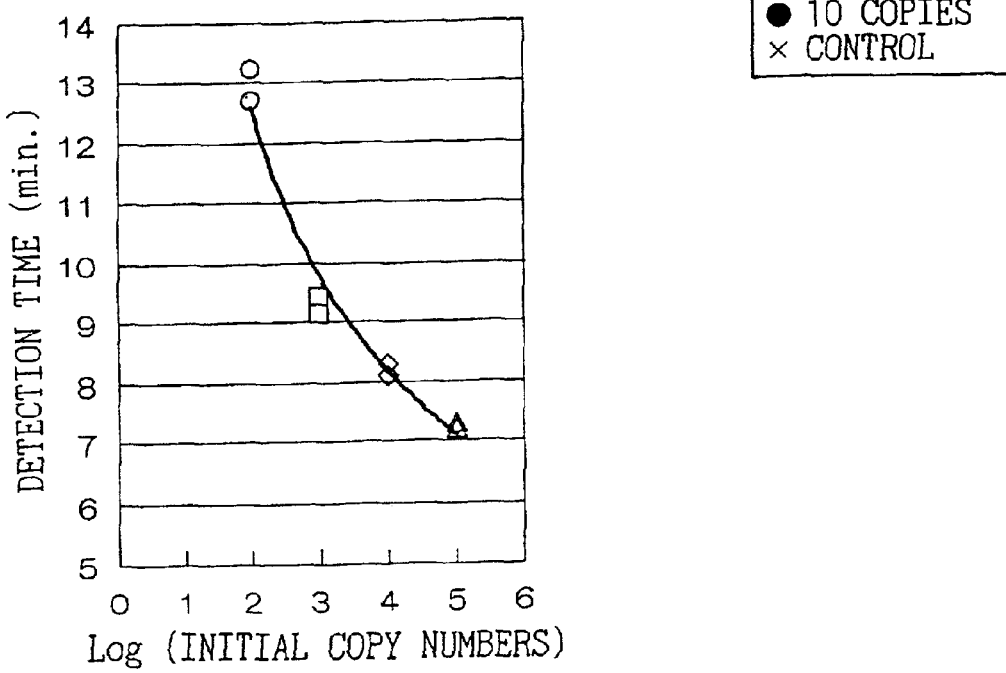
(b)

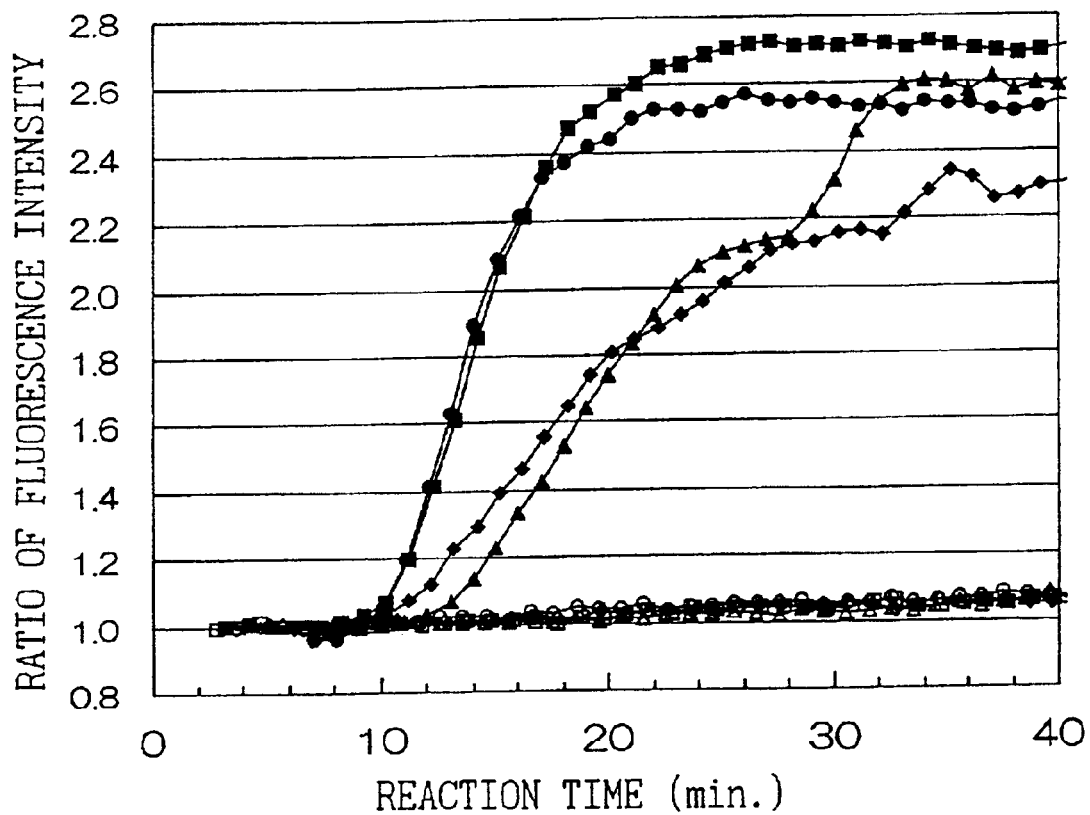

OLIGONUCLEOTIDE FOR DETECTING *SALMONELLA* AND METHOD OF DETECTING *SALMONELLA*

FIELD OF THE INVENTION

The present invention relates to oligonucleotides for detecting mRNA (hereinafter, sometimes referred to as "target RNA") of toxin genes invA or stn of *Salmonella* bacteria, that is commonly known as cause of bacterial food poisoning, and a detection method using the same.

PRIOR ART

Detection and identification of *Salmonella* bacteria in clinical examinations, public health examinations, food evaluations and food poisoning examinations have conventionally conducted via cultivation of *Salmonella* bacteria on a medium to which food or the patient's feces are directly applied or cultivating in a growth medium, followed by cultivation in a selective medium.

Such a culturing method lacks speed because it requires at least 18 hours of cultivation time. Recently, detection methods such as gene amplification methods including PCR methods have been developed to accomplish rapid detection. However, when DNA is the subject to be detected, there is a possibility that a positive result may result from amplification of DNA derived from a killed bacteria contained in the pasteurized food or the like. Moreover, in a detection by electrophoresis following amplification, commonly carried out in the PCR method, there is a possibility that a negative sample will be contaminated due to scattering of amplified products, which may lead to a false positive result.

Due to the fact that RNA is rarely present in killed bacteria, RNA is also detected by a PCR method wherein RNA is preconverted to DNA by a reverse transcription reaction (RT-PCR method). However, since the originally existing DNA is amplified together with RNA, DNA of the killed bacteria is amplified as mentioned above. As a result, there is a possibility that the results are erroneously judged as positive. Removal of the originally existing DNA is required to avoid the false judgment. The detection procedure thus becomes complicated and cannot be conducted rapidly.

NASBA, 3SR, and the like that amplify specific RNA sequences with reverse transcriptase and RNA polymerase are known (see, for example, Japanese Patent Publication No. 2,650,159, with regard to the NASBA method, and European Patent Publication No. 373,960, with regard to the 3SR method). In these methods, the following procedures are carried out: using a specific sequence as a template, a double-stranded DNA including a promoter sequence is synthesized with a primer containing the promoter sequence, reverse transcriptase and Ribonuclease H; this double-stranded DNA is used as a template in synthesizing an RNA containing the specific sequence with an RNA polymerase; and, subsequently, this RNA provides a template in a chain reaction for synthesizing a double-stranded DNA containing the promoter sequence. NASBA, 3SR, and the like allow amplification of only a specific sequence at a constant temperature; moreover, since they allow amplification at a constant temperature, they are considered suitable for automation.

Because the RNA amplification methods such as NASBA and 3SR methods involve relatively low temperature reactions (41° C., for example), the target RNA may form an intramolecular structure that inhibits binding of the primer, which may reduce the reaction efficiency. Therefore, they require subjecting the target RNA to heat denaturation (heat denaturation at 65° C., for example) prior to the amplification reaction so as to destroy the intramolecular structure thereof and thus to improve the primer binding efficiency. As a result, the simplicity and speed of the methods are impaired. Moreover, when the electrophoresis method is to be employed in the detection subsequent to the amplification reactions, the problem of false positive results due to scattering of the amplified product arises, as explained above.

Thus, an object of the present invention is to provide an oligonucleotide capable of complementarily binding to an intramolecular structure-free region of *Salmonella* toxin gene mRNA. That is, an object of the present invention is to provide an oligonucleotide capable of binding to the intramolecular structure-free region and used for amplifying and detecting *Salmonella* toxin gene mRNA and also to provide a detection method used for simple, rapid and highly sensitive clinical examinations, food examinations, food poisoning examinations, and the like, conducted by amplifying the specific sequence of the target RNA with such an oligonucleotide.

The invention according to embodiment 1 and intended to accomplish the objects relates to an oligonucleotide for detection of *Salmonella* toxin gene invA mRNA, which oligonucleotide is capable of specifically binding to *Salmonella* gene invA mRNA, and comprises at least 10 contiguous bases of any of the sequences listed as SEQ. ID. Nos. 1 to 12.

Moreover, the invention according to embodiment 2 and intended to accomplish the objects relates to an oligonucleotide for detection of *Salmonella* toxin gene stn mRNA, which oligonucleotide is capable of specifically binding to *Salmonella* toxin gene stn mRNA, and comprises at least 10 contiguous bases of any of the sequences listed as SEQ. ID. Nos. 13 to 18.

Furthermore, the invention according to embodiment 3 and intended to accomplish the objects relates to a process of amplifying *Salmonella* gene invA mRNA, wherein a specific sequence of *Salmonella* gene invA mRNA present in a sample is used as a template for synthesis of a cDNA employing an RNA-dependent DNA polymerase, the RNA of the formed RNA/DNA hybrid is digested by Ribonuclease H to produce a single-stranded DNA, the single-stranded DNA is then used as a template for production of a double-stranded DNA having a promoter sequence capable of transcribing RNA comprising the specific sequence or the sequence complementary to the specific sequence employing a DNA-dependent DNA polymerase, the double-stranded DNA produces an RNA transcription product in the presence of an RNA polymerase, and the RNA transcription product is then used as a template for oDNA synthesis employing the RNA-dependent DNA polymerase, the amplification process being characterized by employing a first oligonucleotide capable of specifically binding to *Salmonella* gene invA mRNA and comprising at least 10 contiguous bases of any of the sequences listed as SEQ. ID. Nos. 1 to 12 and a second oligonucleotide comprising at least 10 contiguous bases of any of the sequences listed as SEQ. ID. Nos. 19 to 23 and having a sequence homologous to a portion of the *Salmonella* gene invA mRNA sequence to be amplified, where either the first or second oligonucleotide includes the RNA polymerase promoter sequence at the 5' end.

Still furthermore, the invention according to embodiment 4 and intended to accomplish the objects relates to a process of amplifying *Salmonella* gene stn mRNA, wherein a specific sequence of *Salmonella* gene stn mRNA present in a sample is used as a template for synthesis of a cDNA employing an RNA-dependent DNA polymerase, the RNA of the formed RNA/DNA hybrid is digested by Ribonuclease H to produce a single-stranded DNA, the single-stranded DNA is then used as a template for production of a double-stranded DNA having a promoter sequence capable of transcribing RNA comprising the specific sequence or the sequence complementary to the specific sequence employing a DNA-dependent DNA polymerase, the double-stranded DNA produces an RNA transcription product in the presence of an RNA polymerase, and the RNA transcription product is then used as a template for cDNA synthesis employing the RNA-dependent DNA polymerase, the amplification process being characterized by employing a first oligonucleotide capable of specifically binding to *Salmonella* gene stn mRNA, and comprising at least 10 contiguous bases of any of the sequences listed as SEQ. ID. Nos. 13 to 18 and a second oligonucleotide comprising at least 10 contiguous bases of any of the sequences listed as SEQ. ID. Nos. 24 to to 27 and having a sequence homologous to a portion of the *Salmonella* gene stn mRNA sequence to be amplified, where either the first or second oligonucleotide includes the RNA polymerase promoter sequence at the 5' end.

The invention according to embodiment 5 relates to a detection method comprising carrying out the amplification process according to embodiment 3 or 4 in the presence of an oligonucleotide probe capable of specifically binding to the RNA transcription product resulting from the amplification and labeled with an intercalator fluorescent pigment, and measuring changes in the fluorescent properties of the reaction solution, with the proviso that the labeled oligonucleotide has a sequence different from those of the first oligonucleotide and the second oligonucleotide. The invention according to embodiment 6 relates to the detection method according to emdodiment 5, characterized in that the probe is designed so as to complementarily bind to at least a portion of the sequence of the RNA transcription product, and the fluorescent property changes relative to that of a situation where a complex formation is absent. The invention according to emdodiment 7 relates to the detection method according to embodiment 6, characterized in that the probe for detecting the invA mRNA comprises at least 10 contiguous bases of SEQ. ID. No. 28 or its complementary sequence. The invention according to emdodiment 8 relates to the detection method according to emdodiment 6, characterized in that the probe for detecting the stn mRNA comprises at least 10 contiguous bases of SEQ. ID. No. 29 or its complementary sequence. The present invention will be explained below.

An oligonucleotide of the invention capable of specifically binding to *Salmonella* toxin gene invA mRNA and comprising at least 10 contiguous bases of any of the sequences listed as SEQ. ID. Nos. 1 to 12 and an oligonucleotide of the invention capable of specifically binding to *Salmonella* toxin gene stn mRNA and comprising at least 10 contiguous bases of any of the sequences listed as SEQ. ID. Nos. 13 to 18 are characterized by being each capable of specifically binding to a portion that has no steric structure in the target RNA at a relatively low and constant temperature (35 to 50° C.). As a result, the oligonucleotides of the present invention are, for example, useful as primers for practicing a nucleic acid amplifying process such as NASBA and 3SR for the target RNA. In addition, because the oligonucleotides of the present invention are capable of specifically binding to the target RNA at a relatively low and constant temperature (35 to 50° C.), they can be used for the process of amplifying the target RNA by NASBA or 3SR that is carried out to practice the amplifying process in the above temperature range and at a constant temperature (41° C., for example). The use of the oligonucleotides achieves the effect of making unnecessary the denaturation of RNA prior to the practice of such an amplification process as mentioned above.

The present invention also provides a nucleic acid amplification process for amplifying a specific sequence of the target RNA and a method for detecting an RNA transcription product formed in the nucleic acid amplification process. For example, in the amplification process of the NASBA method, a specific sequence of RNA present in a sample is used as a template for synthesis of a cDNA employing an RNA-dependent DNA polymerase, the RNA of the RNA/DNA hybrid is digested by Ribonuclease H to produce a single-stranded DNA, the single-stranded DNA is then used as a template for production of a double-stranded DNA having a promoter sequence capable of transcribing RNA comprising the specific sequence or the sequence complementary to the specific sequence employing a DNA-dependent DNA polymerase, the double-stranded DNA produces an RNA transcription product in the presence of an RNA polymerase, and the RNA transcription product is then used as a template for cDNA synthesis employing the RNA-dependent DNA polymerase. The process of amplifying *Salmonella* toxin gene invA mRNA provided by the present invention is characterized by employing a first oligonucleotide capable of specifically binding to *Salmonella* gene invA mRNA and comprising at least 10 contiguous bases of any of the sequences listed as SEQ. ID. Nos. 1 to 12 and a second oligonucleotide comprising at least 10 contiguous bases of any of the sequences listed as SEQ. ID. Nos. 19 to 23 and having a sequence homologous to a portion of the mRNA sequence to be amplified, where either the first or second oligonucleotide includes the RNA polymerase promoter sequence at the 5' end.

Furthermore, the process of amplifying *Salmonella* toxin gene stn mRNA provided by the present invention is characterized by employing a first oligonucleotide capable of specifically binding to the mRNA and comprising at least 10 contiguous bases of any of the sequences listed as SEQ. ID. Nos. 13 to 18 and a second oligonucleotide comprising at least 10 contiguous bases of any of the sequences listed as SEQ. ID. Nos. 24 to 27 and having a sequence homologous to a portion of the mRNA sequence to be amplified, where either the first or second oligonucleotide includes the RNA polymerase promoter sequence at the 5' end.

There are no particular restrictions on the RNA-dependent DNA polymerase, the DNA-dependent DNA polymerase and the ribonuclease H to be used in the amplification process of the present invention. For example, two or three types of enzymes each having the relevant activity may be used. However, AMV reverse transcriptase that has all of these types of activity is most preferably used. Moreover, although the RNA polymerase to be used in the amplification process of the present invention is not particularly restricted, T7 phage RNA polymerase or SP6 phage RNA polymerase is preferably used.

In the amplification process of the present invention, an oligonucleotide that is complementary to the region adjacent to and overlapping with the 5' end region of the specific sequence (bases 1 to 10) of the target RNA sequence is added, and the target RNA is cleaved with Ribonuclease H at the 5' end region of the specific sequence to give the initial template for nucleic acid amplification, thereby allowing amplification of RNA even when the specific sequence is not positioned at the 5' end. The oligonucleotide used for the cleaving may, for example, be any of those of SEQ. ID. Nos. 1 to 12 for *Salmonella* toxin gene invA mRNA, and SEQ. ID. Nos. 13 to 18 for *Salmonella* toxin gene stn mRNA (provided that it differs from the one used as the first oligonucleotide in the amplification process). In addition, the oligonucleotide for cleaving is preferably chemically modified (for example, aminated) at the 3' hydroxyl group in order to prevent an extension reaction from the 3' end.

The detection method provided by the present invention is characterized by carrying out the amplification process as explained above in the presence of an oligonucleotide probe labeled with an intercalator fluorescent pigment, and measuring changes in the fluorescent properties of the reaction solution. Examples of the oligonucleotide probe include one in which the intercalator fluorescent pigment is bonded to a phosphorus atom in the oligonucleotide through a linker. The probe is characterized in that when it forms a double-stranded chain with the amplification product, separation analysis is not required because the intercalator portion intercalates into the double-stranded chain portion to vary the fluorescent characteristics (Ishiguro, T. et al. (1996), Nucleic Acids Res. 24 (24) 4992–4997).

The probe sequence is not critical so long as it has a sequence complementary to at least a portion of the amplification product. However, the probe sequence is preferably one comprising at least 10 contiguous bases of the sequence listed as SEQ. ID. No. 28 for *Salmonella* toxin gene invA mRNA, and one comprising at least 10 contiguous bases of the sequence listed as SEQ. ID. No. 29 for *Salmonella* toxin gene stn mRNA. Moreover, chemical modification (for example, glycolic acid addition) at the 3' end hydroxyl group of the probe is preferred in order to inhibit an extension reaction based on the probe used as a primer.

It becomes possible to amplify and detect RNA comprising a specific sequence of *Salmonella* toxin gene invA and stn mRNA or a sequence complimentary to the specific sequence thereof in a single tube at a constant temperature and in a single step by carrying out the amplification process in the presence of the probe, as explained above, and, thus, the amplification process is easily automated.

BRIEF DESCRIPTION OF THE DRAWINGS

FIG. 3 shows the results obtained in Example 3 for samples prepared from the *Salmonella* invA mRNA standard with an initial RNA amount between $10^1$ copies/30 µl and $10^5$ copies/30 µl. Upper panel (a) is a fluorescence profile exhibiting the fluorescence increase ratio that increases with the reaction time-course formation of RNA. Lower panel (b) is a calibration curve exhibiting the relationship between the logarithm of the initial RNA amount and the detection time (time at which the relative fluorescence reaches 1.2). It was demonstrated that RNA with initial copies of $10^2$ copies/30 µl can be detected by a reaction for about 13 minutes, and that there is a correlation between the initial RNA amount and the detection time.

FIG. 5 shows the results obtained in Example 5 using samples prepared from the *Salmonella* stn mRNA standard with an initial RNA amount of $10^4$ copies/30 µl, exhibiting the fluorescence increase ratio that increases with the reaction time-course formation of RNA. RNA in an amount of $10^4$ copies/30 µl could be detected by a reaction for about 11 to 15 minutes for any of the combinations of primers. ▲: Fluorescence monitoring employing combination (i) (sample: $10^4$ copies); △: Fluorescence monitoring employing combination (i) (control); ●: Fluorescence monitoring employing combination (j) (sample: $10^4$ copies); ○: Fluorescence monitoring employing combination (j) (control); ◆: Fluorescence monitoring employing combination (k) (sample: $10^4$ copies); ◇: Fluorescence monitoring employing combination (k) (control); ■: Fluorescence monitoring employing combination (l) (sample: $10^4$ copies); and □: Fluorescence monitoring employing combination (l) (control).

EXAMPLES

Figure 1:
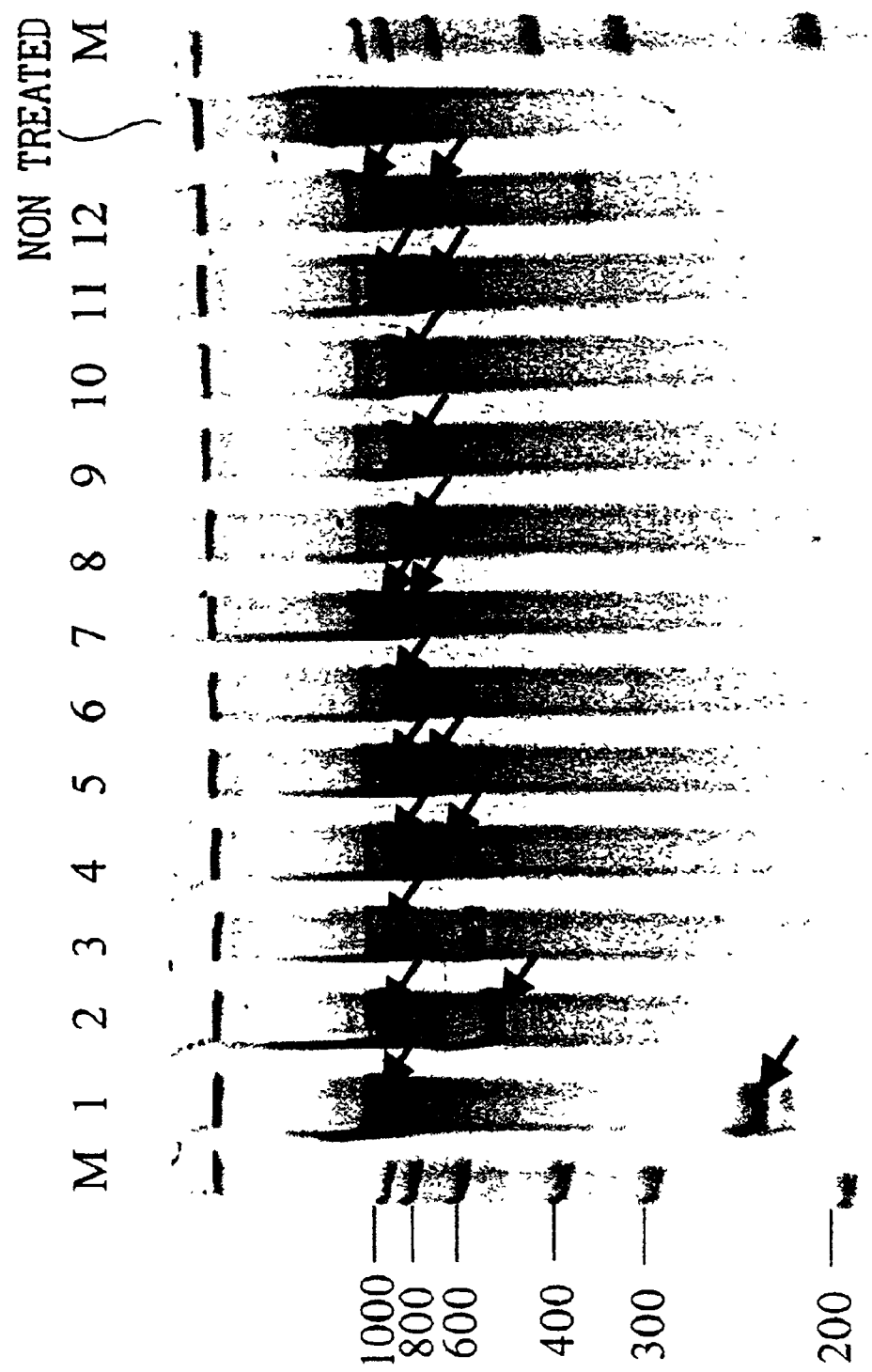
FIG. 1 is an electrophoresis photograph (black and white, negative) of a urea-modified 6% PAGE for samples prepared by conducting the cleavage experiment of Example 1 on *Salmonella* toxin gene invA mRNA standard at 41° C. using oligo-1 to oligo-12 and RNase H. Lane Nos. 1 to 12 correspond to oligo-1 to -12, respectively. M indicates markers. Arrows indicate bands showing specific cleavages.

The present invention will now be explained in greater detail by way of examples, with the understanding that the invention is not limited by the examples.

Example 1

An oligonucleotide which specifically binds to *Salmonella* toxin gene invA mRNA at 41° C. was selected.

(1) PCR was carried out on the region of base Nos. 104 to 2052 of the base sequence of *Salmonella* toxin gene invA (Galan, J. E. et al., J. Bacteriol., 174, 4338–4349 (1992), US GenBank Registered No. M 90846) using a forward primer to which the promoter sequence of T7 RNA polymerase was added at the 5' end and having a sequence homologous to the above base Nos. 104 to 122, and a reverse primer having a sequence complementary to the above base Nos. 2029 to 2052.

(2) The above PCR product was used as a template in preparing a standard RNA by a transcription reaction employing T7 RNA polymerase (manufactured by Takara Shuzo Co., Ltd.). The PCR-produced template was then digested with a DNA polymerase (manufactured by Takara Shuzo Co., Ltd.), and the standard RNA was purified using CHROMA SPIN™ 100 (manufactured by Toyobo Co., Ltd.).

(3) The standard RNA was quantified by ultraviolet absorption at 260 nm, and then diluted to a concentration of 0.45 pmol/µl with an RNA diluent (10 mM Tris-HCl (pH 8.0), 0.1 mM EDTA, 1 mM DTT, 0.5 U/µl RNase Inhibitor).

(4) A reaction solution in an amount of 9.0 µl having the following composition was dispensed into 0.5 ml PCR tubes (Gene Amp Thin-Walled Reaction Tubes™, manufactured by Perkin-Elmer Co., Ltd.).

Reaction Solution Composition 20.0 mM Tris-HCl buffer (pH 7.5)

20.0 mM potassium chloride 10.0 mM magnesium chloride 0.1 mM DTT 0.1 mM EDTA 0.9 µM standard RNA 2.0 µM oligonucleotide (oligonucleotide having any of the sequences listed below being used)

(Oligo-1): SEQ. ID. No. 1

(Oligo-2): SEQ. ID. No. 2

(Oligo-3): SEQ. ID. No. 3

(Oligo-4): SEQ. ID. No. 4

(Oligo-5): SEQ. ID. No. 5

(Oligo-6): SEQ. ID. No. 6

(Oligo-7): SEQ. ID. No. 7

(Oligo-8): SEQ. ID. No. 8

(Oligo-9): SEQ. ID. No. 9

(Oligo-10): SEQ. ID. No. 10

(Oligo-11): SEQ. ID. No. 11

(Oligo-12): SEQ. ID. No. 12

Distilled water for adjusting volume (5) The reaction solutions were then incubated at 41° C. for 5 minutes, and then 1 µl of 0.1 U/µl RNase H (manufactured by Takara Shuzo Co., Ltd.) was added thereto (RNase H: an enzyme that cleaves RNA of a double-stranded DNA/RNA).

(6) Subsequently, the PCR tubes were incubated at 41° C. for 15 minutes.

(7) Urea-modified polyacrylamide gel (acrylamide concentration: 6%; urea: 7 M) electrophoresis was conducted to confirm the cleaved fragments following the reaction. Dyeing following the electrophoresis was carried out with SYBR Green™ II (manufactured by Takara Shuzo Co., Ltd.). Upon binding of the oligonucleotide to the specific sequence of the standard RNA (target RNA), RNA of the double stranded DNA/RNA was cleaved by RNase H. As a result, a characteristic band could be observed.

The results of the electrophoresis are shown in FIG. 1. When the oligonucleotide specifically binds to the standard RNA, the standard RNA will be digested in this binding region, yielding a digestion product having a characteristic chain length. Table 1 shows the position and expected band chain lengths resulting when the oligonucleotide specifically binds to the standard RNA. Cleavages at expected positions were confirmed for Oligo-1 to Oligo-12. It was demonstrated that the oligonucleotides firmly bind to the standard RNA, namely, *Salmonella* toxin gene invA mRNA, at 41° C. and in a constant state.

TABLE 1

| Oligonucleotide | Position[1] | Expected cleaved band lengths (base) |
| --- | --- | --- |
| Oligo-1 | 225 | 225, 1724 |
| Oligo-2 | 518 | 518, 1431 |
| Oligo-3 | 569 | 569, 1380 |
| Oligo-4 | 705 | 705, 1244 |
| Oligo-5 | 742 | 742, 1207 |
| Oligo-6 | 781 | 781, 1168 |
| Oligo-7 | 881 | 881, 1068 |
| Oligo-8 | 922 | 922, 1027 |
| Oligo-9 | 955 | 955, 994 |
| Oligo-10 | 985 | 985, 964 |
| Oligo-11 | 1235 | 1235, 714 |
| Oligo-12 | 1279 | 1279, 670 |

Note:
[1]The position designates the 5' end number of the oligonucleotide which binds to the invA mRNA standard (1949 base).

Example 2

An RNA amplification reaction was carried out using an oligonucleotide probe which specifically binds to *Salmonella* toxin gene invA.

(1) The above *Salmonella* toxin gene invA mRNA was diluted to a concentration of $10^4$ copies/5 µl with an RNA diluent (10 mM Tris-HCl (pH 8.0), 1 mM EDTA, 0.5 U/µl RNase Inhibitor (manufactured by Takara Shuzo Co., Ltd.), 5 mM DTT). In the control testing sections, only the diluent was used (Negative).

(2) A reaction solution in an amount of 20.8 µl having the following composition was dispensed into 0.5 ml PCR tubes (Gene Amp Thin-Walled Reaction Tubes™, manufactured by Perkin-Elmer Co., Ltd.). The above RNA sample in an amount of 5 µl was added.

Reaction Solution Composition (each concentration designating a concentration in a final reaction solution in an amount of 30 µl)

60 mM Tris-HCl buffer (pH 8.6)

13 mM magnesium chloride 90 mM potassium chloride

39 U RNase Inhibitor 1 mM DTT 0.25 mM of each of dATP, dCTP, dGTP and dTTP 3.6 mM ITP 3.0 mM of each of ATP, CTP, GTP and UTP 0.16 µM first oligonucleotide 1.0 µM second oligonucleotide 1.0 µM third oligonucleotide

13% DMSO

Distilled water for adjusting volume (3) An RNA amplification reaction was carried out as explained below using oligonucleotides having a sequence listed in Table 2 as the first, second and third oligonucleotides.

(4) A solution was prepared in step (2) so that the combination of the first, second and third oligonucleotides became one as listed in Table 2.

(5) After incubating the above reaction solution for 5 minutes at 41° C., 4.2 µl of an enzyme solution having the following composition was added.

Enzyme Solution Composition (each concentration designating a concentration in a final reaction solution in an amount of 30 µl)

1.7% sorbitol

3 μg bovine serum albumin

142 U T7 RNA polymerase (Gibco)

8 U AMV-Reverse Transcriptase (Takara Shuzo Co., Ltd.)

Distilled water for adjusting volume (6) Subsequently the PCR tubes were incubated at 41° C. for 30 minutes.

(7) In order to identify the RNA amplified portion following the reaction, agarose gel (agarose concentration of 4%) electrophoresis was performed. Dyeing following the electrophoresis was performed with SYBR Green™ II (manufactured by Takara Shuzo Co., Ltd.). When an oligonucleotide binds to the specific portion of the target RNA, the RNA portion between the second and third oligonucleotides is amplified, thereby enabling observation of a characteristic band.

Figure 2:
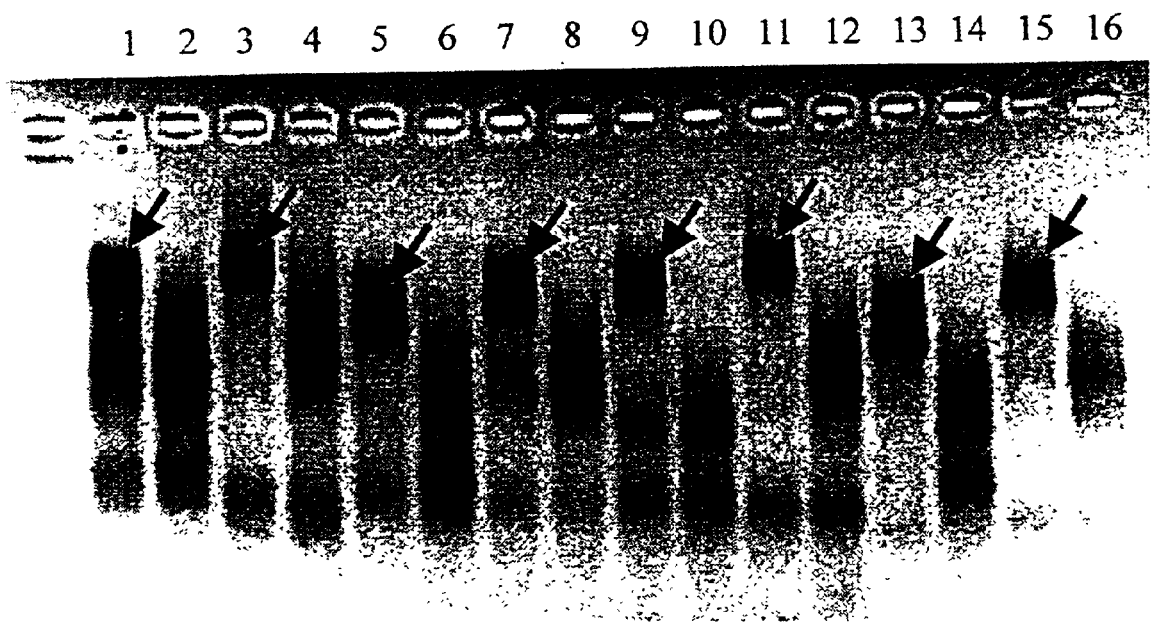
FIG. 2 is an electrophoresis photograph (4% agarose gel) for samples prepared from the RNA amplification reaction of *Salmonella* toxin gene invA mRNA standard in Example 2, with an initial RNA amount of $10^4$ copies/30 µl, using oligonucleotide probes combinations (a) to (h) listed in Table 2. Lanes 1, 2 show the results for combination a); lanes 3, 4 are for combination b); lanes 5, 6 are for combination c); lanes 7, 8 are for combination d); lanes 9, 10 are for combination e); lanes 11, 12 are for combination f); lanes 13, 14 are for combination g); and lanes 15, 16 are for combination h), respectively, wherein lanes 2, 4, 6, 8, 10, 12, 14 and 16 are controls (diluent alone is used in place of the RNA samples.) Arrows indicate specific amplified bands. A characteristic band could be confirmed for any of the combinations.

The results of the electrophoresis are shown in FIG. 2. The chain lengths of the specific bands amplified in the reaction are shown in Table 2. In the RNA amplification reactions using the combinations of oligonucleotides shown in Table 2, a specific band could be confirmed in any of the combinations. Accordingly, it was demonstrated that these combinations are effective in detecting the target RNA.

TABLE 2

| Combination | First oligonucleotide | Second oligonucleotide | Third oligonucleotide | Amplification product chain length (base) |
|---|---|---|---|---|
| (a) | 2S | 2F5 | 4R | 206 |
| (b) | 2S | 2F5 | 5R | 243 |
| (c) | 3S | 3F5 | 4R | 155 |
| (d) | 3S | 3F5 | 5R | 192 |
| (e) | 5S | 5F5 | 8R | 199 |
| (f) | 2S | 2F10 | 5R | 206 |
| (g) | 3S | 3F10 | 4R | 155 |
| (h) | 3S | 3F10 | 5R | 192 |

Table 2 shows the combinations of the first, second and third oligonucleotides used in the present example, as well as the chain lengths of the amplified specific bands resulting from the RNA amplification reactions using these combinations. The 3' end hydroxyl group of each first oligonucleotide base sequence was aminated. In each second oligonucleotide base sequence, the region of the $1^{st}$ "A" to the $22^{nd}$ "A" from the 5' end corresponds to the T7 promoter region, and the subsequent region from the $23^{rd}$ "G" to the $28^{th}$ "A" corresponds to the enhancer sequence.

First Oligonucleotide
   2S (SEQ. ID. No. 2)
   3S (SEQ. ID. No. 3)
   5S (SEQ. ID. No. 5)
Second Oligonucleotide
   2F5 (SEQ. ID. No. 19)
   3F5 (SEQ. ID. No. 20)
   5F5 (SEQ. ID. No. 21)
   2F10 (SEQ. ID. No. 22)
   3F10 (SEQ. ID. No. 23)
Third Oligonucleotide
   4R (SEQ. ID. No. 4)
   5R (SEQ. ID. No. 5)
   8R (SEQ. ID. No. 8)

Example 3

Detection in a various number of initial copies of *Salmonella* toxin gene invA mRNA was carried out using combinations of oligonucleotides according to the present invention.

(1) The same standard RNA as in Example 1 was diluted to concentrations ranging from $10^5$ copies/5 μl to $10^2$ copies/5 μl with an RNA diluent (10 mM Tris-HCl (pH 8.0), 1 mM EDTA, 0.5 U/μl RNase Inhibitor (manufactured by Takara Shuzo Co., Ltd.), 5 mM DTT). In the control testing sections, only the diluent was used (Negative).

(2) A reaction solution in an amount of 20.8 μl having the following composition was dispensed into 0.5 ml PCR tubes (Gene Amp Thin-Walled Reaction Tubes™, manufactured by Perkin-Elmer Co., Ltd.). The above RNA sample in an amount of 5 μl was added.

Reaction Solution Composition (each concentration designating a concentration in a final reaction solution in an amount of 30 μl)

60 mM Tris-HCl buffer (pH 8.6)
   17 mM magnesium chloride
   90 mM potassium chloride
   39 U RNase Inhibitor
   1 mM DTT
   0.25 mM of each of dATP, dCTP, dGTP and dTTP
   3.6 mM of ITP
   3.0 mM of each of ATP, CTP, GTP and UTP
   0.16 μM first oligonucleotide (3S (SEQ. ID. No. 3) in Table 2, wherein its 3' end hydroxyl group is aminated)
   1.0 μM second oligonucleotide (3F10 (SEQ. ID. No. 23) in Table 2)
   1.0 μM third oligonucleotide (4R (SEQ. ID. No. 4) in Table 2)
   25 nM intercalator fluorescent pigment-labeled oligonucleotide (SEQ. ID. No. 28, labeled with an intercalator fluorescent pigment at the phosphorus atom between the $13^{th}$ "A" and the $14^{th}$ "A" from the 5' end, and modified with a glycol group at its 3' end hydroxyl group)
   13% DMSO
   Distilled water for adjusting volume (3) After incubating the above reaction solution for 5 minutes at 41° C., 4.2 μl of an enzyme solution having the following composition and pre-incubated for 2 minutes at 41° C. was added.

Enzyme Solution Composition (each concentration designating a concentration in a final reaction solution in an amount of 30 μl)

1.7% sorbitol
   3 μg bovine serum albumin
   142 U T7 RNA polymerase (Gibco)
   8 U AMV-Reverse Transcriptase (Takara Shuzo Co., Ltd.)
   Distilled water for adjusting volume (4) The PCR tube was then incubated at 41° C. using a direct-measurable fluorescence spectrophotometer equipped with a temperature controller, and the reaction solution was periodically measured at an excitation wavelength of 470 nm and a fluorescent wavelength of 510 nm. FIG. 3 (upper panel) shows the time-course changes in the fluorescence increase ratio (fluorescence intensity at predetermined time/background fluorescence intensity) of the sample, where enzyme was added at 0 minute. FIG. 3 (lower panel) shows the relationship between the logarithm of the initial RNA amount and the detection time (time at which the relative fluorescence reaches the negative sample's average value plus 3 standard deviations; i.e., the time to reach 1.2). The initial RNA amount was between $10^1$ copies/30 μl and $10^5$ copies/30 μl.

FIG. 3 shows that $10^2$ copies were detected in about 13 minutes. A fluorescent profile and a calibration curve both depending on the initial concentration of the labeled RNA were obtained, indicating that it is possible to quantify the target RNA present in unknown samples. This demonstrates that rapid, highly sensitive detection of invA mRNA is possible by this method.

Example 4

An oligonucleotide which specifically binds to *Salmonella* toxin gene stn mRNA at 41° C. was selected.

(1) PCR was carried out on the region of base Nos. 346 to 1092 of the base sequence of *Salmonella* toxin gene stn (Chopra, A. K. et al., Microb. Pathog., 16, 85–98 (1994), US GenBank Registered No. L 16014) using a forward primer to which the promoter sequence of T7 RNA polymerase was added at the 5' end having a sequence homologous to the above base Nos. 346 to 369, and a reverse primer having a sequence complementary to the above base Nos. 1076 to 1092.

(2) The above PCR product was used as a template for preparation of the standard RNA by a transcription reaction employing T7 RNA polymerase (manufactured by Takara Shuzo Co., Ltd.). The PCR-produced template was digested with a DNA polymerase (manufactured by Takara Shuzo Co., Ltd.), and the standard RNA was purified using CHROMA SPIN™ 100 (manufactured by Toyobo Co., Ltd.).

(3) The standard RNA was quantified by ultraviolet absorption at 260 nm, and then diluted to a concentration of 0.45 pmol/µl with an RNA diluent (10 mM Tris-HCl (pH 8.0), 0.1 mM EDTA, 1 mM DTT, 0.5 U/µl RNase Inhibitor).

(4) A reaction solution in an amount of 9.0 µl having the following composition was dispensed into PCR tubes (volume of 0.5 ml, Gene Amp Thin-Walled Reaction Tubes™, manufactured by Perkin-Elmer Co., Ltd.).

Reaction Solution Composition
20.0 mM Tris-HCl buffer (pH 7.5)
20.0 mM potassium chloride
10.0 mM magnesium chloride
0.1 mM DTT
0.1 mM EDTA
0.9 µM standard RNA
2.0 µM oligonucleotide (an oligonucleotide having any of the sequences listed below being used)
  (Oligo-13): SEQ. ID. No. 13
  (Oligo-14): SEQ. ID. No. 14
  (Oligo-15): SEQ. ID. No. 15
  (Oligo-16): SEQ. ID. No. 16
  (Oligo-17): SEQ. ID. No. 17
  (Oligo-18): SEQ. ID. No. 18
Distilled water for adjusting volume (5) The reaction solutions were then incubated at 41° C. for 5 minutes, and then 1 µl of 0.1U/µl RNase H (manufactured by Takara Shuzo Co., Ltd.; an enzyme that cleaves RNA of a double-stranded DNA/RNA) was added thereto.

(6) Subsequently, the PCR tubes were incubated at 41° C. for 15 minutes.

(7) Urea-modified polyacrylamide gel (acrylamide concentration: 6%; urea: 7 M) electrophoresis was conducted to confirm the cleaved fragments following the reaction. Dyeing following the electrophoresis was carried out with SYBR Green™ II (manufactured by Takara Shuzo Co., Ltd.). Upon binding of the oligonucleotide to the specific sequence of the standard RNA (target RNA), RNA of the double stranded DNA/RNA is cleaved by RNase H. As a result, a characteristic band could be observed.

Figure 4:
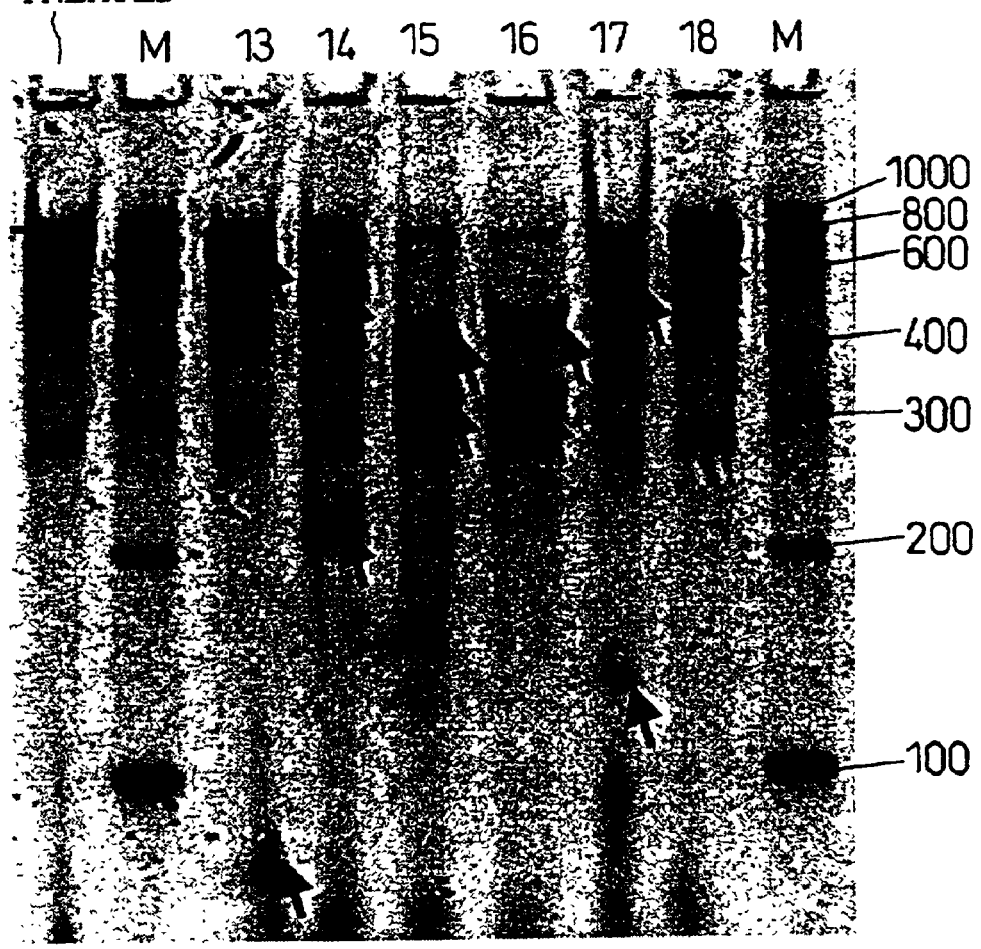
FIG. 4 is an electrophoresis photograph (black and white, negative) of a urea-modified 6% PAGE for samples prepared by conducting the cleavage experiment of Example 4 on *Salmonella* toxin gene stn mRNA standard at 41° C. using oligo-13 to oligo-18 and RNase H. Lane Nos. 13 to 18 correspond to oligo-13 to -18, respectively. M indicates markers. Arrows indicate bands showing specific cleavages.

The results of the electrophoresis are shown in FIG. 4. When the oligonucleotide specifically binds to the standard RNA, the standard RNA will be digested in this binding region, yielding a digestion product having a characteristic chain length. Table 3 shows the position and expected band chain lengths when an oligonucleotide specifically binds to the standard RNA. Cleavages at expected positions were confirmed for Oligo-13 to Oligo-18. It was demonstrated that the oligonucleotides firmly bind to *Salmonella* toxin gene stn mRNA at 41° C. and in a constant state.

TABLE 3

| Oligonucleotide | Position[1] | Expected cleaved band lengths (base) |
| --- | --- | --- |
| Oligo-13 | 59 | 59, 688 |
| Oligo-14 | 191 | 191, 556 |
| Oligo-15 | 311 | 311, 436 |
| Oligo-16 | 421 | 421, 326 |
| Oligo-17 | 642 | 642, 105 |
| Oligo-18 | 671 | 671, 76 |

Note:
[1]The position designates the 5' end number of an oligonucleotide which binds to the stn mRNA standard (747 base).

Example 5

Combinations of oligonucleotides according to the present invention were used for detection of different initial copy numbers of *Salmonella* toxin gene stn mRNA.

(1) The same standard RNA of *Salmonella* toxin gene stn mRNA as in Example 4 was diluted to a concentration of $10^4$ copies/5 µl with an RNA diluent (10 mM Tris-HCl (pH 8.0), 1 mM EDTA, 0.5 U/µl RNase Inhibitor (manufactured by Takara Shuzo Co., Ltd.), 5 mM DTT). In the control testing sections, only the diluent was used (Negative).

(2) A reaction solution in an amount of 20.8 µl having the following composition was dispensed into 0.5 ml PCR tubes (Gene Amp Thin-Walled Reaction Tubes™, manufactured by Perkin-Elmer Co., Ltd.). The above RNA sample in an amount of 5 µl was added.

Reaction Solution Composition (each concentration designating a concentration in a final reaction solution in an amount of 30 µl)
60 mM Tris-HCl buffer (pH 8.6)
17 mM magnesium chloride
90 mM potassium chloride
39 U RNase Inhibitor
1 mM DTT
0.25 mM of each of dATP, dCTP, dGTP and dTTP
3.6 mM ITP
3.0 mM of each of ATP, CTP, GTP and UTP
0.16 µM first oligonucleotide (combination in Table 4, hydroxyl group at the 3' end being aminated)
1.0 µM second oligonucleotide (combination in Table 4)
1.0 µM third oligonucleotide (combination in Table 4)
25 nM intercalator fluorescent pigment-labeled oligonucleotide (SEQ. ID. No. 29, labeled with an intercalator fluorescent pigment at the phosphorus atom between the $12^{th}$ "A" and the $13^{th}$ "A" from the 5' end, and modified with a glycol group at its 3' end hydroxyl group)
13% DMSO
Distilled water for adjusting volume (3) After incubating the above reaction solution for 5 minutes at 41° C., 4.2 μl of an enzyme solution having the following composition and pre-incubated for 2 minutes at 41° C. was added.

Enzyme Solution Composition (each concentration designating a concentration in a final reaction solution in an amount of 30 μl)

1.7% sorbitol

3 μg bovine serum albumin

142 U T7 RNA polymerase (Gibco)

8 U AMV-Reverse Transcriptase (manufactured by Takara Shuzo Co., Ltd.)

Distilled Water for Adjusting Volume (4) The PCR tube was then incubated at 41° C. using a direct-measurable fluorescence spectrophotometer equipped with a temperature controller, and the reaction solution was periodic measured at an excitation wavelength of 470 nm and a fluorescent wavelength of 510 nm.

FIG. 5 shows the time-course changes in the fluorescence increase ratio (fluorescence intensity at predetermined time/background fluorescence intensity) of the sample, where enzyme was added at 0 minute.

Defining the detection time as a time at which the relative fluorescence exceeds 1.2, FIG. 5 then shows that $10^4$ copies can be detected in about 11 to 15 minutes. This demonstrates that rapid, highly sensitive detection of stn mRNA is possible by the method.

TABLE 4

| Combination | First oligonucleotide | Second oligonucleotide | Third oligonucleotide | Amplification product chain length (base) |
|---|---|---|---|---|
| (i) | B1S | B1F5 | B4R | 233 |
| (j) | B3S | B3F5 | B4R | 120 |
| (k) | B1S | B1F10 | B4R | 233 |
| (l) | B3S | B3F10 | B4R | 120 |

Table 4 shows the combinations of the first, second and third oligonucleotides used in the present example, as well as the chain lengths of the amplified characteristic bands resulting from the RNA amplification reactions using these combinations. The 3' end hydroxyl group of each first oligonucleotide base sequence was aminated. In each second oligonucleotide base sequence, the region of the $1^{st}$ "A" to the $22^{nd}$ "A" from the 5' end corresponds to the T7 promoter region, and the subsequent region from the $23^{rd}$ "G" to the $28^{th}$ "A" corresponds to the enhancer sequence.

First oligonucleotide
  B1S (SEQ. ID. No. 13)
  B3S (SEQ. ID. No. 14)
Second oligonucleotide
  B1F5 (SEQ. ID. No. 24)
  B3F5 (SEQ. ID. No. 25)
  B1F10 (SEQ. ID. No. 26)
  B3F10 (SEQ. ID. No. 27)
Third oligonucleotide
  B4R (SEQ. ID. No. 15)

Results

As explained above, the present invention provides oligonucleotides capable of complementarily binding to an intramolecular structure-free region of *Salmonella* toxin gene invA and stn mRNA, and a detection method using the oligonucleotides. Moreover, the present invention provides oligonucleotides for detecting *Salmonella* toxin gene invA and stn mRNA, namely, oligonucleotide primers and oligonucleotide probes used for nucleic acid amplification methods. Because the oligonucleotides provided by the present invention are capable of specifically binding to the target RNA at a relatively low and constant temperature, they are particularly suitable as primers used for a process of amplifying the target RNA.

The amplification processes and detection methods provided by the present invention use oligonucleotides favorable to the process of amplifying the target RNA as explained above. As a result, the present invention achieves the effect of making heat-denaturing of the target in advance unnecessary when the amplification process is to be carried out at a relatively low and constant temperature.

What is claimed is:

1. A process of amplifying *Salmonella* gene invA mRNA having a specific sequence, comprising
obtaining a sample comprising *Salmonella* gene invA mRNA
synthesizing cDNA employing an RNA-dependent DNA polymerase resulting in an RNA/DNA hybrid,
digesting the RNA of the RNA/DNA hybrid with Ribonuclease H to produce a single-stranded DNA,
producing a double-stranded DNA having a promoter sequence capable of transcribing RNA comprising said specific sequence or a sequence complementary to said specific sequence employing a DNA-dependent DNA polymerase, wherein said single-stranded DNA is the template for said producing and wherein said double-stranded DNA produces an RNA transcription product in the presence of an RNA polymerase, and
synthesizing cDNA comprising annealing an oligonucleotide primer pair consisting of the sequence of SEQ ID NO: 4 and SEQ ID NO: 23 to said RNA transcription product and amplifying said cDNA by employing said RNA-dependent DNA polymerase, where either primer includes an RNA polymerase promoter sequence at the 5' end.

2. The process according to claim 1, which is a detection method, wherein said amplifying is performed in the presence of an oligonucleotide probe which has a sequence that is complementary to at least a portion of the RNA transcription product, is labeled with an intercalator fluorescent pigment, and has a sequence different from said oligonucleotide primer pair, wherein changes in the fluorescent properties of the intercalator are measured.

3. The detection method according to claim 2, wherein said probe for detecting said invA mRNA comprises at least 10 contiguous bases of SEQ. ID. No. 28 or its complementary sequence.

4. The process of claim 1, wherein said annealing is at a temperature ranging from 35 to 50° C.

5. The process of claim 1, wherein said amplifying said cDNA is at a temperature ranging from 35 to 50° C.

6. The process of claim 5, wherein said amplifying said cDNA is at a constant temperature.

7. The process of claim 1, wherein the process is performed using a single enzyme having RNA-dependent DNA polymerase, DNA-dependent DNA-polymerase, and ribonuclease H activity.

8. The process of claim 7, wherein said enzyme is AMV reverse transcriptase.

9. The process of claim 1, wherein said RNA polymerase is a T7 phage RNA polymerase.

10. The detection method according to claim 2, wherein said intercalator fluorescent pigment is bonded to a phosphorus atom in the oligonucleotide probe through a linker.

11. The detection method according to claim 5, wherein said oligonucleotide probe is modified at the 3' hydroxyl group such that extension from said probe is inhibited.

12. The detection method according to claim 11, wherein said oligonucleotide probe is modified at the 3' hydroxyl group by addition of a glycolic acid.

13. The detection method according to claim 3, wherein said oligonucleotide probe is modified at the 3' hydroxyl group such that extension from said probe is inhibited.

14. The detection method according to claim 13, wherein said oligonucleotide probe is modified at the 3' hydroxyl group by addition of a glycolic acid.

* * * * *

SEQUENCE LISTING

<160> NUMBER OF SEQ ID NOS: 29

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
agacgactgg tactgatcga    20

<210> SEQ ID NO 2
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
aggaaccgta aagctggctt    20

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
taatgatgcc ggcaatagcg                                          20

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
atcaacaatg cggggatctg                                          20

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
atttacgcgg gtcacgataa                                          20

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
ctgcgtcatg atattccgcc                                          20

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
ccgataaaat aacaaaaacc                                          20

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
tgcttcacgg aatttaaaat                                          20

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
tttgctggtt ttaggtttgg                                           20

<210> SEQ ID NO 10
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
tttttcctca atactgagcg                                           20

<210> SEQ ID NO 11
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
ccgtaaattg ttcaacacgg                                           20

<210> SEQ ID NO 12
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
gacttcatcg gaataattta                                           20

<210> SEQ ID NO 13
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
aaggtgaaaa gtattgaggg                                           20

<210> SEQ ID NO 14
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
gatagcggga aagggatcgc                                           20

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
aggctgactc aggtgctgtt                                           20

<210> SEQ ID NO 16

```
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
atattattac tcactccctg                                               20

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
ggggcatctg gcggcgggcg                                               20

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
atgaagcgta aagaaaagct                                               20

<210> SEQ ID NO 19
<211> LENGTH: 48
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
aattctaata cgactcacta tagggagatt cctttgacgg tgcgatga                48

<210> SEQ ID NO 20
<211> LENGTH: 48
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
aattctaata cgactcacta tagggagagg catcattatt atctttgt                48

<210> SEQ ID NO 21
<211> LENGTH: 48
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
aattctaata cgactcacta tagggagata aatggcgata cggataat                48

<210> SEQ ID NO 22
<211> LENGTH: 48
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
```
aattctaata cgactcacta tagggagata cggttccttt gacggtgc        48

<210> SEQ ID NO 23
<211> LENGTH: 48
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
aattctaata cgactcacta tagggagaca ttattatctt tgtgaact        48

<210> SEQ ID NO 24
<211> LENGTH: 48
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
aattctaata cgactcacta tagggagaac cttaatcgcg ccgccatg        48

<210> SEQ ID NO 25
<211> LENGTH: 48
<212> TYPE: DNA
<213> ORGANISM: ARTIFICIAL SEQUENCE
<220> FEATURE:
<223> OTHER INFORMATION: SYNTHETIC DNA

<400> SEQUENCE: 25
aattctaata cgactcacta tagggagact atcggtaaca gtgatgat        48

<210> SEQ ID NO 26
<211> LENGTH: 48
<212> TYPE: DNA
<213> ORGANISM: ARTIFICIAL SEQUENCE
<220> FEATURE:
<223> OTHER INFORMATION: SYNTHETIC DNA

<400> SEQUENCE: 26
aattctaata cgactcacta tagggagatt ttcaccttaa tcgcgccg        48

<210> SEQ ID NO 27
<211> LENGTH: 48
<212> TYPE: DNA
<213> ORGANISM: ARTIFICIAL SEQUENCE
<220> FEATURE:
<223> OTHER INFORMATION: SYNTHETIC DNA

<400> SEQUENCE: 27
aattctaata cgactcacta tagggagatc ccgctatcgg taacagtg        48

<210> SEQ ID NO 28
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 28
tcagcatggt ataagtagac agggcg        26

<210> SEQ ID NO 29
<211> LENGTH: 20
<212> TYPE: DNA

```
<213> ORGANISM: ARTIFICIAL SEQUENCE
<220> FEATURE:
<223> OTHER INFORMATION: SYNTHETIC DNA

<400> SEQUENCE: 29
agacgactgg tactgatcga                                               20
```